US005601364A

United States Patent [19]
Ume

[11] Patent Number: 5,601,364
[45] Date of Patent: Feb. 11, 1997

[54] METHOD AND APPARATUS FOR MEASURING THERMAL WARPAGE

[75] Inventor: Ifeanyi C. Ume, Stone Mountain, Ga.

[73] Assignee: Georgia Tech Research Corporation, Atlanta, Ga.

[21] Appl. No.: 259,434

[22] Filed: Jun. 14, 1994

[51] Int. Cl.⁶ ............ G01N 17/00; G01N 3/60; G01B 11/24; G01B 11/30
[52] U.S. Cl. ............ 374/57; 250/237 G; 356/374; 356/376
[58] Field of Search ............ 374/57; 356/374, 356/376; 250/237 G

[56] References Cited

U.S. PATENT DOCUMENTS

| | | | |
|---|---|---|---|
| 1,346,793 | 7/1920 | Bunnell et al. | 219/480 |
| 3,292,418 | 12/1966 | Oehme et al. | 374/57 |
| 3,566,078 | 2/1971 | Krackow | 219/486 |
| 3,614,237 | 10/1971 | Kyle et al. | 356/120 |
| 3,762,818 | 10/1973 | Johnson et al. | 356/120 |
| 4,011,430 | 3/1977 | Witkin et al. | 219/486 |
| 4,158,742 | 6/1979 | Aldrich et al. | 13/20 |
| 4,172,993 | 10/1979 | Leach | 324/158 |
| 4,317,985 | 3/1982 | Wilson | 219/210 |
| 4,378,701 | 4/1983 | Mountain et al. | 374/47 |
| 4,426,160 | 1/1984 | Couderc | 374/45 |
| 4,449,032 | 5/1984 | Frerking | 219/210 |
| 4,632,291 | 12/1986 | Rahn et al. | 228/9 |
| 4,650,333 | 3/1987 | Crabb et al. | 356/376 |
| 4,752,140 | 6/1988 | Cielo et al. | 374/55 |
| 4,963,025 | 10/1990 | Blackmon et al. | 3536/376 |
| 4,989,991 | 2/1991 | Pecot et al. | 374/133 |
| 5,000,574 | 3/1991 | Scotese et al. | 356/376 |
| 5,053,604 | 10/1991 | Escaravage et al. | 219/483 |
| 5,103,078 | 4/1992 | Boykin et al. | 219/494 |
| 5,148,003 | 9/1992 | Haj-Ali-Ahmadi et al. | 219/388 |
| 5,152,607 | 10/1992 | Ibar | 374/53 |
| 5,182,439 | 1/1993 | Burkett et al. | 219/412 |
| 5,307,152 | 4/1994 | Boehnlein et al. | 356/376 |

*Primary Examiner*—Diego F. F. Gutierrez
*Attorney, Agent, or Firm*—Deveau, Colton & Marquis

[57] ABSTRACT

A method and apparatus for measuring thermally induced warpage in test elements such as printed wiring boards and printed wiring assemblies, including a heating chamber having a transparent window and support structure for supporting a printing wiring board in an observation orientation and position parallel to the transparent window. A glass grating placed adjacent the window and a light source shines through the window onto the printed wiring board under test. A camera is positioned for capturing images of shadow moiré fringes formed over time as the oven heats up the printed wiring board or printed wiring assembly to simulate actual process conditions. A computer is used for controlling operation of the apparatus and for evaluating the captured images of the moiré fringes in relation to the temperature as a function of time.

15 Claims, 3 Drawing Sheets

5,601,364

METHOD AND APPARATUS FOR MEASURING THERMAL WARPAGE

TECHNICAL FIELD

This invention generally relates to a method and apparatus for measuring warpage in a test element and more particularly relates to a method and apparatus for on-line measurement of thermally induced warpage using a shadow moiré technique.

BACKGROUND OF THE INVENTION

It is known to simulate processing conditions and to perform measurements under the simulated processing conditions to determine how a particular material will react under actual processing conditions. For example, U.S. Pat. No. 4,426,160 of Couderc discloses a method and apparatus for optically measuring the deformation of a material (e.g., pitch) under heat to determine the wetting power of the material. Also, U.S. Pat. No. 3,292,418 of Oehme et al. discloses a method and apparatus that simulates the conditions (i.e., high temperatures) encountered in drying equipment employed with printing presses to obtain indications of blistering characteristics prior to printing. U.S. Pat. No. 4,989,991 of Pecot et al. discloses a method and apparatus for calibrating the emissivity characteristics of a semiconductor wafer by sensing the actual temperature of a semiconductor wafer with a thermal sensor and, at the same time, measuring the temperature of the wafer by optical pyrometry under processing conditions that ideally would be the same for all wafers to be processed in a processing chamber.

It is also known in the art to use optical techniques to determine the design or shape of an object. Kyle et al., U.S. Pat. No. 3,614,237, disclose a method and apparatus for measuring the contour of a surface by illuminating the surface through a periodically repetitive image structure, thereby casting a shadow of the structure onto the surface. The surface and the shadow cast thereon are viewed visually by an observer or are photographed through the structure as moiré fringes. The contour of the surface is then determined from the moiré fringes.

Crabb et al., U.S. Pat. No. 4,650,333, disclose a system for detecting printed circuit wiring defects and for measuring the height of circuit features. Non-uniformity and variations of the substrate surface due to bending or warpage can be accounted for when measuring the height of the circuit features. The substrate and circuit features are illuminated by an energy source and a scanner receives energy reflected from the substrate and the circuit features and generates a signal which varies in accordance with the intensity of the reflected energy. An analyzer receives the signal generated by the scanner and derives therefrom a measurement representative of the height of the circuit features relative to the substrate.

In attempting to determine the thermal warpage developed in printed wiring boards during assembly/manufacturing operations, some difficulties arise. Firstly, making direct measurements of the warpage in the printed wiring board during such operations is problematical inasmuch as the board typically is moved along a conveyor through one or more oven zones to facilitate soldering, with the oven enclosures restricting access to the board. Thus, making a direct measurement of the warpage in printed wiring boards in process may be impractical. Secondly, in attempting to simulate actual process conditions using a test station, it can be difficult to change the temperature in the test station quickly enough and accurately enough to adequately simulate the actual process conditions existing along the conveyor. Thirdly, even if one can adequately replicate the process conditions of the conveyor within a stationary work station, the task of accurately measuring the warpage in a given board remains a daunting one.

Accordingly, it can be seen that a need yet remains for a method and apparatus for measuring thermal warpage in test devices, elements, or specimens (especially in printed wiring boards) which accurately simulates actual process temperature conditions and which attains accuracy in measuring the thermal warpage. It is to the provision of such a method and apparatus that the present invention is primarily directed.

SUMMARY OF THE INVENTION

Briefly described, in a preferred form the present invention comprises a method for measuring thermally induced warpage in a device, element, or specimen. The method preferably is employed using a heating chamber for housing and heating the specimen, an illumination source, a grating, and a camera. The method includes the steps of placing the specimen in the heating chamber and illuminating the specimen with light from the illumination source directed through the grating and onto the specimen, thereby forming shadow moiré fringes on the specimen. The method also includes the steps of capturing a first image of the shadow moiré fringes with the camera and heating the specimen in the heating chamber to cause the temperature of the specimen to follow a desired temperature profile over an interval of time. Subsequent images of shadow moiré fringes are captured with the camera over the interval of time while also recording the temperature of the specimen over the same time interval. The warpage of the specimen is then determined as a function of temperature by evaluating the first image of the shadow moiré fringes, the subsequent images of the shadow moiré fringes captured over the interval of time, and the temperature of the specimen over the interval of time.

In another preferred form, the invention comprises an apparatus for measuring thermally induced warpage in a device, element, or specimen, especially in printed wiring boards and printed wiring assemblies, including a heating chamber having a transparent window formed therein and means for selectively controlling the temperature of the heating chamber. The apparatus also includes means for supporting the specimen in an observation orientation and observation position within the heating chamber and a grating is supported in parallel relationship to the observation orientation and is maintained a selected distance from the observation position within the heating chamber. The apparatus further includes a light source for illuminating the specimen through the grating such that shadow moiré fringes are formed on the specimen. A camera is positioned for capturing images of the shadow moiré fringes. Means are provided for monitoring the temperature of the specimen over time. Also, evaluation means are provided for determining the warpage of the specimen by evaluating the captured images of the shadow moiré fringes in relation to the temperature of the specimen as monitored over time.

The method and apparatus according to the invention accurately simulates actual process temperature conditions and attains accuracy in measuring the thermal warpage. It also is simple in its construction and operation. Furthermore, it provides a low cost means of evaluating thermally induced warpage in the surface of any test element, such as printed wiring boards (and printed wiring board assemblies).

Accordingly, it is a primary object of the present invention to provide a method and apparatus for on-line measurement of thermally induced warpage which is durable in construction, simple in operation, and economical in manufacture.

It is another object of the present invention to provide a method and apparatus for measuring thermally induced warpage which accurately simulates actual process temperature conditions.

It is another object of the present invention to provide a method and apparatus for measuring thermal warpage which attains good accuracy in measuring the thermal warpage.

These and other objects, features, and advantages of the present invention will become apparent upon reading the following specification in conjunction with the accompanying drawing figures.

BRIEF DESCRIPTION OF THE DRAWING FIGURES

DETAILED DESCRIPTION

The present invention is directed to a method and apparatus for measuring thermally induced warpage in the surface of any desired test device, element, or specimen. For purposes of illustration, description of the invention is presented in a preferred form in connection with printed wiring boards or printed wiring assemblies.

Figure 1:
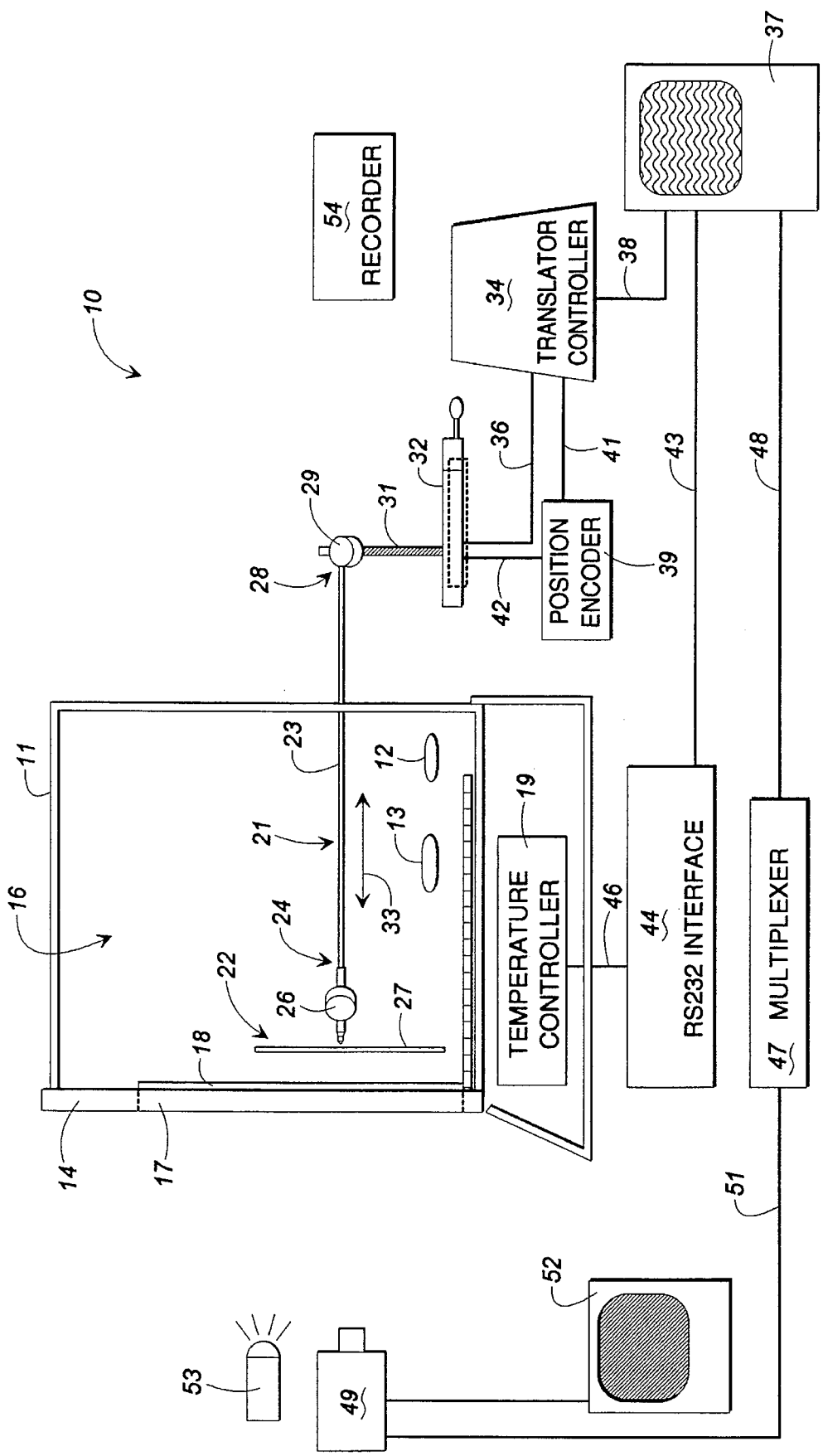
FIG. 1 is a schematic diagram of an apparatus fix measuring thermal warpage in test specimens, such as printed wiring boards and printed wiring assemblies, according to a preferred form of the invention.

Referring now in detail to the drawing figures, wherein like reference numerals depict like parts throughout the several views, FIG. 1 shows an apparatus 10 for measuring thermal warpage in a printed wiring board or printed wiring assembly, according to a first preferred form of the invention. Apparatus 10 includes an oven or heating chamber 11 having a first constant-or fixed-output heating element 12 and a variable output heating element 13. The oven 11 also includes a door 14 for providing access to the interior region 16 of the oven 11. The door 14 also includes a light transparent window 17. A grating 18 is positioned behind and parallel to, and in close proximity to, window 17. A controllable temperature controller 19 controls the operation and output of the heating elements 12 and 13 to control the temperature within the oven. In a prototype apparatus actually constructed and operated, the temperature controller 19 is a unit made by Honeywell Corporation (Model No. DC3003-0-10A-1-00-0111). Preferably, the oven is capable of being operated at between, at least, operating temperatures of 25° C. and 300° C.

A support assembly indicated at 21 is provided for supporting a printed wiring board or printed wiring assembly in an observation position indicated generally at 22 within the oven. The supporting assembly 21 includes an elongate support rod 23 which is made of a material having a low coefficient of thermal expansion, such as Invar®, for maintaining the printed wiring board in an essentially stationary position despite temperature changes within the heating chamber 11. The elongate support rod 23 extends from externally of oven 11 to internally thereof. A first end indicated generally at 24 of elongate support rod 23 is positioned within the interior region 16 of the oven 11 and supports a support bracket 26, which in turn supports the printed wiring board or printed wiring assembly 27. A second end, generally indicated at 28, of the elongate support rod 23 is positioned externally of the oven 11 and is connected to a right angle support bracket 29. The right angle support bracket 29 is in turn supported by an upright stanchion 31 securely mounted to a motorized linear translator 32. The linear translator 32 is provided for translating the elongate support rod 23 back and forth in the direction of direction arrows 33. Through the translator 32, precise control of position of the printed wiring board or primed wiring assembly relative to the grating 18 can be effected. A translator controller 34 (X-Y controller) having an RS232 interface is electronically connected to the translator 32 by electrical cabling 36 for effecting control of the translator. The translator controller 34 also is electronically coupled to a control computer 37 via electrical cabling 38. The translator controller 34 is also electrically connected to a position encoder 39 having a readout or display for displaying the position of the translator via electrical cabling 41 and electrical cabling 42.

The control computer 37 communicates with the temperature controller 19 for effecting control of the temperature controller 19 via electrical cabling 43, a converter and RS232 interface 44 and electrical cabling 46. The control computer 37 receives video signal information from a multiplexer 47 via electrical cabling 48. The multiplexer 47 receives video signals from a camera or other image capturing means 49 via electrical cabling 51. Preferably, the camera 49 comprises a charged coupled device ("CCD") type video camera. Preferably, the CCD camera 49 also outputs a signal to a video monitor 52 for viewing by the test operator. A white light source, schematically indicated at 53, is directed toward and illuminates the printed wiring board or printed wiring assembly 27 through the grating 18 for creating shadow moiré fringe patterns. Preferably, the light source 53 is a collimated white light source. Thermocouples (unshown) are used to monitor the temperature of the printed wiring board or printed wiring assembly 27 within the oven 11 and are electrically connected with X-Y recorder 54 by unshown electrical cabling for recording the actual temperature of the printed wiring board over time.

Figure 2:
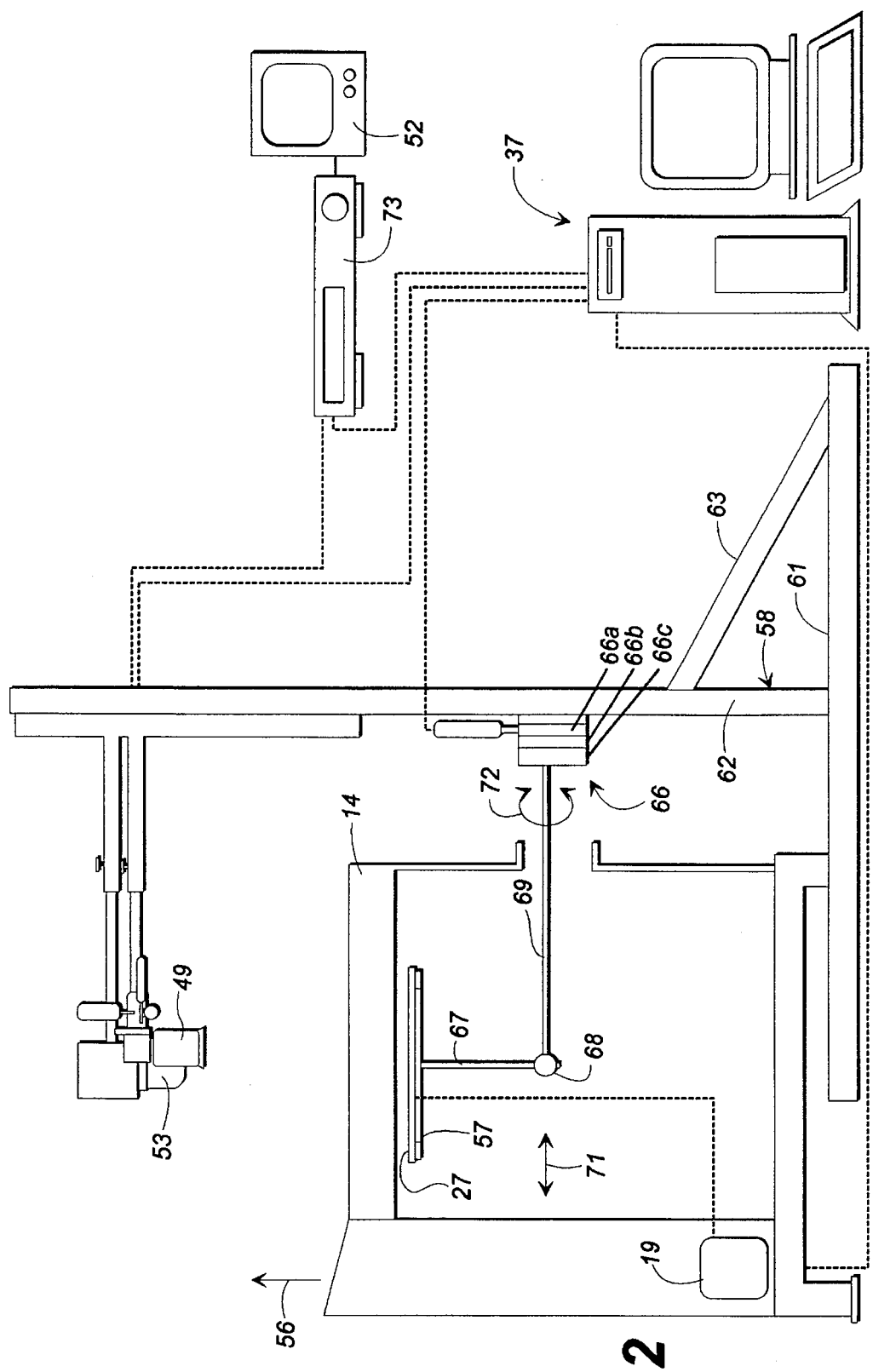
FIG. 2 is a schematic diagram of an apparatus for measuring thermal warpage according to a second preferred form of the invention.

FIG. 2 shows a second embodiment, similar to that shown in FIG. 1, with some notable differences. For example, in FIG. 2 the oven is rotated 90 degrees so that the door 14 faces upwardly in the direction of direction arrow 56. This arrangement places the printed wiring board or printed wiring assembly 27, which is secured in a holder 57, in a horizontal orientation, rather than a vertical orientation. FIG. 2 also shows that the oven is securely mounted to a large support framework 58, which also supports the camera 49 and light source 53, thereby maintaining accurate positioning of the camera 49 relative to the oven, and ultimately relative to the printed wiring board 27. The support frame 58 includes a floor (beam) section 61, an upright stanchion or post 62 rigidly secured thereto, and a strut 63 extending between the floor section 61 and the upright post 62 at an angle for stiffening the post 62 against deflection.

Additionally, FIG. 2 shows the use of a positioning mechanism indicated generally at 66 for adjusting the position and orientation of the printed wiring board or printed wiring assembly 27. In this regard, the holder 57 for the printed wiring board or printed wiring assembly 27 is supported by an upright post 67 secured to a bracket 68, which in turn is secured to an elongate mounting rod 69. Both the upright post 67 and the elongate mounting rod 69 are made from material having a low coefficient of thermal expansion, as described previously. The positioning mechanism 66 includes means for effecting linear translation in the direction of direction arrows 71, rotation in the direction of direction arrows 72, and inclination (relative to horizontal orientation) of the printed wiring board or printed wiring assembly 27. Preferably, the positioning mechanism 66 includes equipment designated as MR80 Linear Stage, TG Inclination Stage and TR Rotation Stage, respectively, all manufactured by Newport/Klinger of Irvine, Calif.

Preferably, as shown in FIG. 2, the apparatus also includes a video cassette recorder 73 for recording images of the shadow moiré fringes that result.

Figure 3:
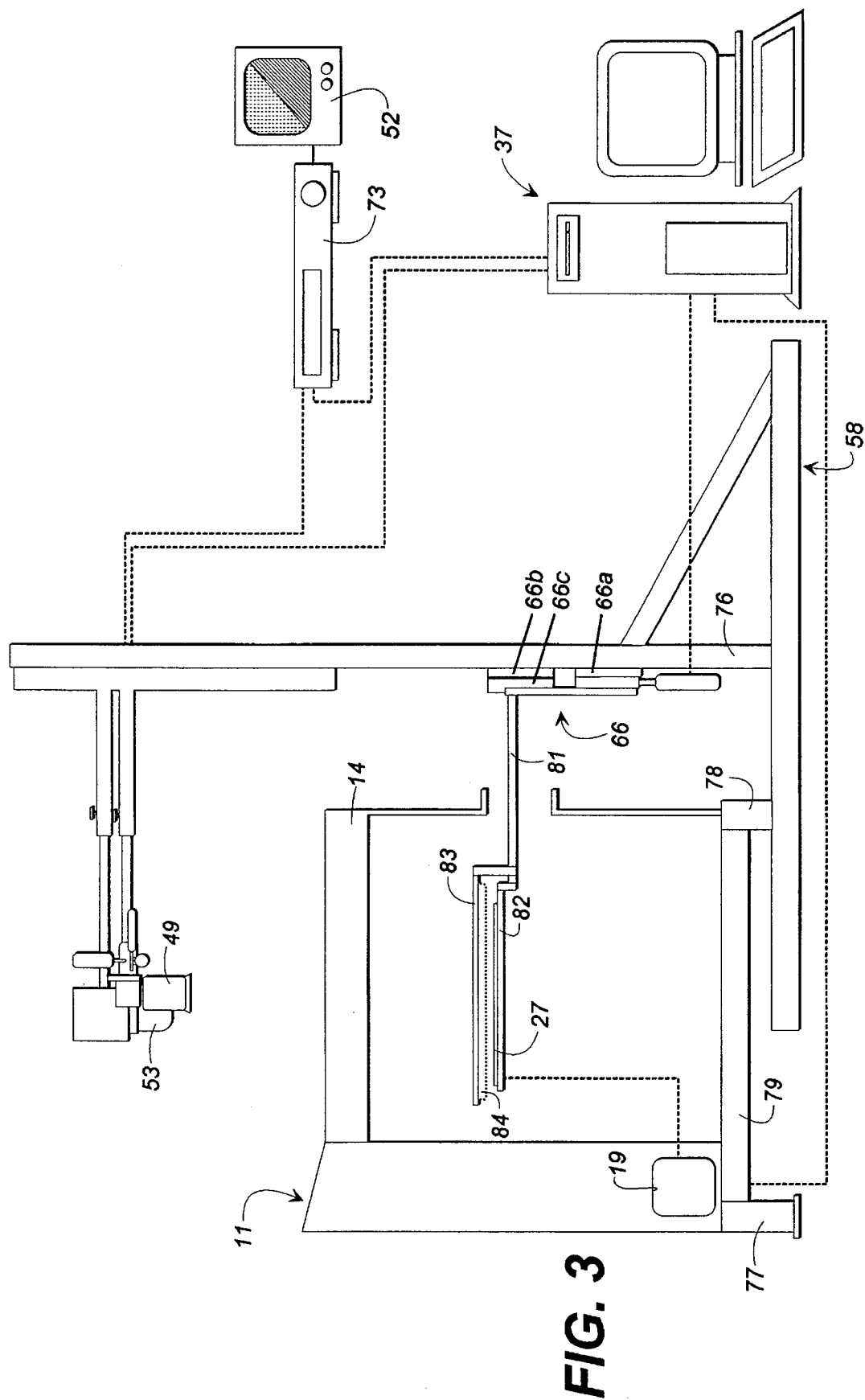
FIG. 3 is a schematic diagram of an apparatus for measuring thermal warpage according to a third preferred form of the invention.

FIG. 3 shows another embodiment wherein the support frame 58 is in another form and comprises upright posts, such as upright posts 76, 77, and 78 and a floor section 79. FIG. 3 also shows a preferred means for supporting a printed wiring board (or assembly) 27 in an observation orientation and observation position within the heating chamber 11. The means for supporting preferably includes the previously described positioning mechanism 66, an Invar® mounting rod 81, a first support platform 82, and a second support platform 83. Second support platform 83 supports an interchangeable grating 84 within the oven 11 (rather than being placed in the oven door). Also, first support platform 82 supports a specimen (e.g., a printed wiring assembly or printed wiring board). One advantage to this arrangement is that the distance from the specimen to the grating can be tightly controlled.

OPERATION

In use, the oven 11 is heated to a preset elevated temperature. The oven door 14 is opened and a printed wiring board or printed wiring assembly 27 to be tested preferably after having been stored at room temperature is quickly placed inside. The heating elements 12, 13, which in the prototype actually constructed and used are ceramic heaters, are used to accelerate the heating of the oven to follow a selected temperature profile. In this regard, the variable-output heating element 13, which is connected to a variable transformer, is utilized to help simulate the environment considered, such as for wave soldering or infrared reflow processing. A multi-channel X-Y recorder 54 is used to record the time dependent temperature of the thermocouples that are placed at different locations on the printed wiring board or printed wiring assembly. Temperature profile curves are obtained from these thermocouple readouts. While the time dependent temperatures are being recorded, the camera 49 is used to capture the images of the dynamic shadow moiré fringes. The shadow moiré fringes change as the board 27 is warping due to the rise in temperature in the board. A frame grabber is used to capture the images at different intervals of time and the images are digitized and stored in the control computer. Preferably, the frame grabber captures a first image of the shadow moiré fringes essentially immediately after placement of the printed wiring board or printed wiring assembly 27 in the heating chamber 11. At the end of the evaluation, the data is converted to obtain two and three-dimensional representations of the warpage of the printed wiring board or printed wiring assembly 27. An absolute or relative warpage can be determined based on the number of fringes at the time and temperature at which the image is obtained. The warpage of the printed wiring board or printed wiring assembly 27 is calculated according to the following:

$$W = NP/(\tan A + \tan B)$$

where W is the out-of-plane deformation of the board;

A is the incident angle of light;

B is camera viewing angle;

N is the fringe order; and

P is the pitch of the grating.

This method and apparatus provides excellent resolution and accuracy. It also allows warpage due to thermal distortion to be measured in real time. This technique accurately simulates actual process temperature conditions and is simple in its construction and operation. Also, it provides a low cost means of evaluating thermally induced warpage.

While the invention has been disclosed in preferred forms, it will be apparent to those skilled in the art that many modifications, additions, and deletions may be made therein. For example, while a video camera is disclosed specifically, a still camera could be employed. Such modifications, additions, and deletions fall within the spirit and scope of the invention as set forth in the appended claims.

What is claimed is:

1. A method for measuring thermally induced warpage in specimens using a heating chamber for housing and heating a specimen, an illumination source, a grating, and a camera, the method comprising the steps of:

placing and supporting the specimen in the heating chamber;

illuminating the specimen with light from the illumination source directed through the grating onto the specimen, thereby forming shadow moiré fringes on the specimen;

capturing a first image of the shadow moiré fringes with the camera;

heating the specimen in the heating chamber to cause the temperature of the specimen to follow a desired temperature profile over a period of time;

capturing subsequent images of shadow moiré fringes with the camera over the period of time while also recording the temperature of the specimen over the period of time; and determining the warpage of the specimen as a function of temperature by evaluating the first image of shadow moiré fringes, the subsequent images of the shadow moiré fringes captured over the period of time, and the temperature of the specimen recorded over the period of time.

2. A method as claimed in claim 1 wherein the step of placing and supporting the specimen comprises maintaining the specimen in a stationary observation position.

3. A method as claimed in claim 1 wherein the step of determining the warpage is carried out according to the following: $W = NP/(\tan A + \tan B)$, where W is the out-of-plane warpage, N is the fringe order, P is the grating pitch, A is the angle of light incidence, and B is the camera angle.

4. A method as claimed in claim 1 wherein, prior to the step of placing and supporting the specimen in the heating chamber, the heating chamber is preheated to an elevated temperature.

5. A method as claimed in claim 4 wherein the specimen is held at room temperature prior to placement in the heating chamber and wherein the step of capturing a first image of the shadow moiré fringes is carried out essentially immediately after placement of the specimen in the heating chamber.

6. A method as claimed in claim 1 wherein the specimen in which thermally induced warpage is measured is a printed wiring board or printed wiring assembly.

7. An apparatus for measuring thermally induced warpage in specimens comprising:

a heating chamber having a transparent window formed therein;

means for selectively controlling the temperature within said heating chamber;

means for supporting a specimen in an observation orientation, and an observation position within said heating chamber;

a grating supported in parallel relationship to said observation orientation, said grating being a selected distance from said observation position within said heating chamber;

a light source for illuminating the specimen through said grating such that shadow moiré fringes are formed on the specimen;

a camera positioned for capturing images of the shadow moiré fringes;

means for monitoring the temperature of the specimen over time; and evaluation means for determining the warpage of the specimen by evaluating the captured images of the shadow moiré fringes in relation to the temperature of the specimen as monitored over time.

8. An apparatus as claimed in claim 7 wherein said means for supporting a specimen is effective for maintaining the specimen in an essentially stationary position despite temperature changes within said heating chamber.

9. An apparatus as claimed in claim 8 wherein said means for supporting a specimen comprises a support member made of a material having low thermal expansion properties.

10. As apparatus as claimed in claim 7 further comprising means for adjusting the distance from said observation position to said grating.

11. An apparatus as claimed in claim 7 wherein said light source is positioned externally of said heating chamber.

12. An apparatus as claimed in claim 7 wherein said means for supporting a specimen supports the specimen in a vertical orientation.

13. An apparatus as claimed in claim 7 wherein said means for supporting a specimen supports the specimen in a horizontal orientation.

14. An apparatus as claimed in claim 7 wherein said means for selectively controlling the temperature within said heating chamber comprises a fixed-output heating element and a variable-output heating element.

15. An apparatus as claimed in claim 7 wherein the specimen in which thermally induced warpage is measured is a printed wiring board or printed wiring assembly.

* * * * *

EX PARTE REEXAMINATION CERTIFICATE (6585th)
United States Patent
Ume

(10) Number: US 5,601,364 C1
(45) Certificate Issued: Dec. 30, 2008

(54) METHOD AND APPARATUS FOR MEASURING THERMAL WARPAGE

(75) Inventor: Ifeanyi C. Ume, Stone Mountain, GA (US)

(73) Assignee: Georgia Tech Research Corporation, Atlanta, GA (US)

Reexamination Request:
No. 90/007,575, Jun. 6, 2005

Reexamination Certificate for:
| | |
|---|---|
| Patent No.: | 5,601,364 |
| Issued: | Feb. 11, 1997 |
| Appl. No.: | 08/259,434 |
| Filed: | Jun. 14, 1994 |

(51) Int. Cl.
*G01B 11/16* (2006.01)
*G01N 3/60* (2006.01)

(52) U.S. Cl. .................. 374/57; 250/237 G; 356/605
(58) Field of Classification Search .................. None
See application file for complete search history.

(56) References Cited

U.S. PATENT DOCUMENTS

| | | | | |
|---|---|---|---|---|
| 3,128,362 | A | * 4/1964 | Clark et al. | 219/398 |
| 4,313,679 | A | * 2/1982 | Wolff et al. | 356/244 |
| 5,296,683 | A | * 3/1994 | Burkett et al. | 219/497 |
| 5,327,075 | A | * 7/1994 | Hashinaga et al. | 324/158.1 |

OTHER PUBLICATIONS

Excerpts from Jeffrey David Garrett's Master's Thesis entitled "Prediction Of Thermally Induced Printed Wiring Board Warpage," Dated Sep. 1993, Page Excerpts Include Cover Page, Title Page, and pp. 76–91.

Banerjee, K., Yeh, C., Umeagukwu, C., Fulton, R., Martin, T., Stafford, J. and Wyatt, K., "Experimental Investigation of Thermally Induced Warpage of Printed Wiring Boards," American Society of Non-destructive Testing Spring Conference, Oakland, California, Mar. 18–22, 1991.

Yeh, C., Ume, C., Fulton, R., Wyatt, K. and Stafford, J., "Correlation of Analytical and Experimental Approaches to Determination of Thermally Induced Printed Wiring Board (PWB) Warpage," in Handbook of Thermal Stress and Strain in Microelectronic Packaging (Chapter 9), (John H. Lau, Ed.), New York: Van Nostrand Reinhold, Oct. 1993, pp. 305–328.

Yeh, C., Ume, C., Fulton, R., Wyatt, K., and Stafford, J., "Correlation of Analytical and Experimental Approaches to Determine Thermally Induced PWB Warpage", IEEE Transactions on Components, Hybrids and Manufacturing Technology, vol. 16, No. 8, Dec. 1993, pp. 986–995.

Yeh et al., "Experimental and Analytical Investigation of Thermally Induced Warpage for Printed Wiring Boards", 1991 IEEE, pp. 382–387.

Martin et al., "Measurement of Thermally Induced Warpage in Printed Wiring Boards", AMD–Vo. 13/EEP—vol. 1, (Manufacturing processes and Materials Challenges in Microelectronic Packaging (ASME 1991), pp. 43–47.

* cited by examiner

*Primary Examiner*—James Menefee

(57) ABSTRACT

A method and apparatus for measuring thermally induced warpage in test elements such as printed wiring boards and printed wiring assemblies, including a heating chamber having a transparent window and support structure for supporting a printing wiring board in an observation orientation and position parallel to the transparent window. A glass grating placed adjacent the window and a light source shines through the window onto the printed wiring board under test. A camera is positioned for capturing images of shadow moiré fringes formed over time as the oven heats up the printed wiring board or printed wiring assembly to simulate actual process conditions. A computer is used for controlling operation of the apparatus and for evaluating the captured images of the moiré fringes in relation to the temperature as a function of time.

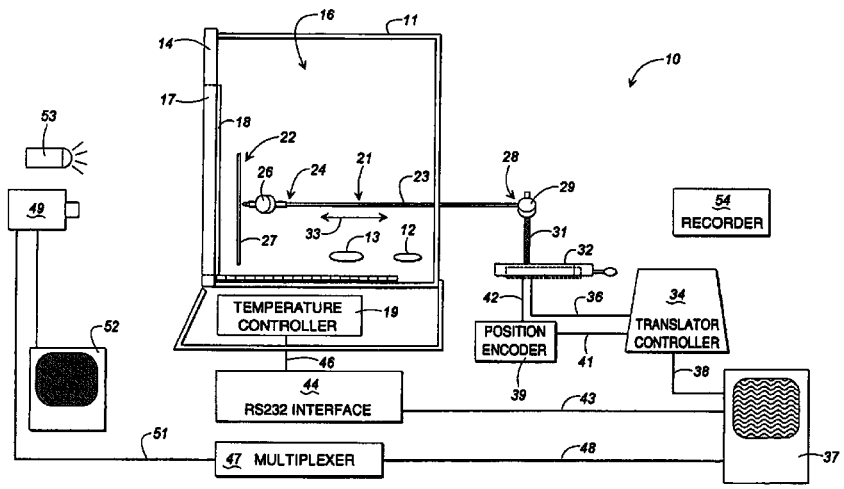

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 9 is cancelled.

Claims 1, 2, 6, 7 and 8 are determined to be patentable as amended.

Claims 3–5 and 10–15, dependent on an amended claim, are determined to be patentable.

New claims 16–24 are added and determined to be patentable.

1. A method for measuring thermally induced warpage in specimens using a heating chamber for housing and heating a specimen, *the specimen defining a surface*, an illumination source, a grating, and a *video* camera, the method comprising the steps of:
   placing and supporting the specimen in the heating chamber;
   illuminating the specimen with light from the illumination source directed through the grating onto the specimen, thereby forming shadow moiré fringes on the specimen, *the grating being spaced apart from the specimen such that a continuous gap is defined between the specimen and the grating*;
   capturing a first image of the shadow moiré fringes with the camera;
   heating the specimen in the heating chamber to cause the temperature of the *surface of the* specimen to follow a desired temperature profile over a period of time;
   *receiving a temperature of the surface of the specimen from a temperature sensor placed external and proximate the surface of the specimen and adjusting heat within the chamber so that the surface temperature of the specimen follows the desired temperature profile;*
   capturing subsequent images of shadow moiré fringes with the *video* camera over the period of time while also recording the temperature of the specimen over the period of time; and
   determining the warpage of the specimen as a function of temperature by evaluating the first image of shadow moiré fringes, the subsequent images of the shadow moiré fringes captured over the period of time, and the temperature of the specimen recorded over the period of time.

2. A method as claimed in claim 1 wherein the step of placing and supporting the specimen comprises maintaining the specimen in a stationary observation position *with a support rod made from a material having a low coefficient of thermal expansion such that the material does not substantially expand in response to being heated.*

6. A method as claimed in claim 1 wherein the specimen in which thermally induced warpage is measured is a printed wiring board or printed wiring *board* assembly.

7. An apparatus for measuring thermally induced warpage in specimens comprising:
   a heating chamber having a transparent window formed therein;
   means for selectively controlling the temperature *of a surface of a specimen* within said heating chamber;
   means for supporting [a] *the* specimen in an observation orientation, and an observation position within said heating chamber;
   a grating supported in parallel relationship to said observation orientation, said grating being a selected distance from said observation position within said heating chamber, *the grating being spaced apart from the specimen such that a continuous gap is disposed between the grating and the specimen*;
   a light source for illuminating the specimen through said grating such that the shadow moiré fringes are formed on the specimen;
   a camera positioned for capturing images of the shadow moiré fringes;
   means for monitoring the temperature of the specimen *coupled to said means for selectively controlling the temperature of the specimen within the heating chamber to achieve specific specimen temperatures* over time, *said means for monitoring positioned external and proximate the surface of the specimen*; and
   evaluation means for determining the warpage of the specimen by evaluating the captured images of the shadow moiré fringes in relation to the temperature of the specimen as monitored over time.

8. An apparatus as claimed in claim 7 wherein said means for supporting a specimen is effective for maintaining the specimen in an essentially stationary position despite temperature changes within said heating chamber, *said means for supporting being formed with a material having a low coefficient of thermal expansion such that said material does not substantially expand when exposed to heat as the specific specimen temperatures are reached thereby enabling the specimen to substantially maintain the essentially stationary position.*

*16. The method of claim 1 the evaluation means comprising a frame grabber to capture images of the surface of the specimen as the surface of the specimen follows the desired temperature profile, the evaluation means being configured to provide multi-dimensional warpage data representative of the surface of the specimen being warped.*

*17. The method of claim 1 further comprising providing a linear translator coupled to the specimen for translating the specimen within the heating chamber, the linear translator configured to control positioning of the specimen within the heating chamber in response to control signals provided by a controller.*

*18. The method of claim 17, further comprising a position encoder coupled to the linear translator, the position encoder configured to display the position of the specimen within the heating chamber.*

*19. The method of claim 1 further comprising providing a plurality of temperature sensors external and proximate the specimen to obtain a plurality of temperature readings at different locations on the surface of the specimen, the sensors being coupled to a data recorder configured to record time dependent temperatures sensed by the sensors.*

20. The apparatus of claim 7 further comprising a temperature sensor proximate and external the specimen as the means for monitoring the temperature of the specimen within the heating chamber.

21. The apparatus of claim 7, the means for supporting the specimen comprising a holder defining a holding surface, said holding surface supporting at least a portion of the specimen.

22. The apparatus of claim 7 further comprising a translator controller configured to control the position of the specimen within the heating chamber, the controller coupled to a positioning mechanism configured to at least one of alter the lateral position of the specimen, the incline position of the specimen, or rotational position of the specimen.

23. The apparatus of claim 22 further comprising a position encoder coupled to the linear translator and the controller, the position encoded configured to display position information of the specimen within the heating chamber.

24. The apparatus of claim 7 further comprising a multi-channel data recorder configured to record time-dependent temperature data provided by the means for monitoring the temperature of the specimen.

* * * * *